United States Patent [19]

Tomblin et al.

[11] Patent Number: 4,617,102

[45] Date of Patent: Oct. 14, 1986

[54] PROCESS AND APPARATUS FOR PURIFYING AND CONCENTRATING DNA FROM CRUDE MIXTURES CONTAINING DNA

[75] Inventors: Graham J. Tomblin, Tappan; Karen B. Wexler, Harrison; John P. Ford, Tappan; Stuart G. Fischer, New York, all of N.Y.

[73] Assignee: Lifecodes Corp., Elmsford, N.Y.

[21] Appl. No.: 714,376

[22] Filed: Mar. 21, 1985

[51] Int. Cl.[4] .......................................... G01N 27/28
[52] U.S. Cl. ................................ 204/299 R; 204/301; 204/182.8
[58] Field of Search ................ 204/299 R, 301, 182.1, 204/182.3, 182.6, 182.8

[56] References Cited

U.S. PATENT DOCUMENTS

| | | | |
|---|---|---|---|
| 3,533,933 | 10/1970 | Strauch | 204/182.8 |
| 3,576,727 | 4/1971 | Evatt | 204/182.8 |
| 3,697,406 | 10/1972 | Svendsen | 204/182.8 X |
| 3,773,648 | 11/1973 | Van Welzen et al. | 204/299 R |
| 3,844,925 | 10/1974 | Stathakos | 204/299 R |
| 3,902,986 | 9/1975 | Nees | 204/299 R X |
| 3,989,612 | 11/1976 | Kragt et al. | 204/299 R X |
| 4,111,785 | 9/1978 | Roskam | 204/299 R |
| 4,479,861 | 10/1984 | Hediger | 204/182.8 |
| 4,545,888 | 10/1985 | Walsh | 204/301 |
| 4,552,640 | 11/1985 | Kartenbeck | 204/301 |

FOREIGN PATENT DOCUMENTS 2148325  5/1985  United Kingdom ............. 204/182.3

OTHER PUBLICATIONS

Clad, A., et al., "A Cheap, Time- and DNA-Saving Device for the Electrophoretic Elution of DNA from Gels", *Analytical Biochemistry*, vol. 124, pp. 299–302, (1982).

Primary Examiner—John F. Niebling
Assistant Examiner—B. J. Boggs, Jr.
Attorney, Agent, or Firm—John F. Ohlandt

[57] ABSTRACT

A process and apparatus for purifying and concentrating DNA, which has relatively high molecular weight, from a crude mixture containing DNA for example from human whole blood samples; the collected DNA is of usable volume and concentration, and is of such purity as to permit conventional restriction by a number of enzymes without the need for further purification. The apparatus consists essentially of an agarose gel disc, typically 5 mm. thick by 31 mm. in diameter, immersed in an electrophoresis buffer solution and supported between two 8 micrometer polycarbonate filters in an electric field. Further, the method involves the loading of a suitably treated sample such as blood lysate onto the top face of the agarose gel disc and then applying an electric field. On the constituent parts of the treated blood, the DNA molecules are the largest with regard to molecular weight. Consequently, their passage through the agarose gel disc, under the force of the electric field, is impeded. All other constituent parts of the treated blood pass relatively rapidly through the disc and are removed, being swept away by flow of the buffer solution. The DNA is then eluted and collected, in concentrated form by application of the electric field, whilst the normal flow of buffer solution between the bottom of the gel matrix and a collection chamber is prevented.

14 Claims, 4 Drawing Figures

PROCESS AND APPARATUS FOR PURIFYING AND CONCENTRATING DNA FROM CRUDE MIXTURES CONTAINING DNA

BACKGROUND OF THE INVENTION

1. Field of the Invention

This invention relates to one general field of extraction of high molecular weight DNA from test samples, particularly from human whole blood.

2. Background Information

Within the field of medical diagnostics there is a growing new methodology that uses DNA as the material for diagnostic tests.

For this type of diagnostic testing to be commercially competitive, overall cost of DNA based tests have to be minimized. One way of achieving lower costs is to reduce man-hours consumed by the various procedures comprising both extraction of DNA from samples and testing and analysis of DNA; in particular, by improving the efficiency of these procedures by incorporating some level of automation.

It will be appreciated, of course, that a variety of testing procedures have been developed. However, some of these that have been described in the art are based on the ability to obtain the DNA in reasonable volume. For example, referring to U.S. Pat. No. 4,391,688 to Hamelin, there is disclosed an electrophoresis system for multiple agarose slab gels. That system involves adding a solution of a mixture of molecules of mixed molecular weights, such as DNA, to wells formed in a horizontal slab gel, after which the gel is treated by electrophoresis to produce localized bands, each being characteristic of a specific molecular weight.

The method or system described in U.S. Pat. No. 4,391,688 is dependent on having a sufficient volume and concentration of DNA readily available. However, it is precisely this lack of easy availability of concentrated DNA that presents a significant difficulty to the use of DNA in diagnostic tests. This is because one of the most time-consuming steps is the procedure used to extract DNA from its source.

Accordingly, a fundamental object of the present invention is to reduce the processing times inherent in the operation of extracting the DNA from test samples and particularly in extracting the DNA from human whole blood samples.

A further major object is to permit the imposition of rigorous quality control on a DNA extraction procedure by means of automation. This reduces administrative costs normally associated with a quality control program.

Another object is to minimize the possibility of random processing errors during a DNA extraction procedure.

Yet another object is to provide an apparatus that is relatively uncomplicated and is easily expandable to large volume extractions in a DNA-based medical diagnostics laboratory.

Still another object is to make the extraction apparatus modifiable for the purposes of extracting DNA from material other than human whole blood.

A design feasibility study conducted by the present inventors has established that automation of the conventional extraction procedure could only be achieved in part, because of a number of steps involving the centrifuging of samples. Typically, five or more centrifuging steps are involved with conventional extraction procedures. Additionally, various aqueous phases have to be removed by means of wide-mouthed pipetting and returned to plastic tubes that held the original samples. The point that bears emphasis is that the complete conventional procedure takes about four days.

Accordingly, other major objects of the present invention are to develop a procedure and apparatus that can extract DNA from whole blood without the need for any centrifuging steps and in the final analysis, to reduce the time for extracting the DNA from about four days, in conventional practice, to approximately five hours.

Since extractions of the kind being discussed, i.e. those involving purifying and concentrating DNA from crude mixtures such as human whole blood, are to be performed on a large scale, the probability of human error is increased. Therefore, the terms of reference for the invention are the designing and building of apparatus that will incorporate a unique and inexpensive system of DNA extraction; further, the provision of apparatus that will reduce the probability of human error.

Accordingly, further objects of the present invention are to provide an automatable or semi-automatable system, such that the operations are traceable and recordable, whereby the status of the process can be monitored in time. Also, to reduce the cost such that DNA-based diagnostic testing can be competitive with other types of testing.

SUMMARY OF THE INVENTION

The above and other objects are fulfilled and implemented by the several features of the present invention. Briefly described, the process of the present invention includes the steps of preparing a test sample and particularly a whole blood lysate sample; followed by the step of placing the sample in apparatus developed in accordance with the present invention, whereby a series of operations are performed that yield a usable and convenient quantity of DNA. The apparatus includes at least one agarose gel disc, typically 5 mm. thick by 31 mm. in diameter. Such disc is immersed in an electrophoresis buffer solution, being supported between two polycarbonate filters, typically 8 micrometer, and situated within an electric field. Means are provided for producing the required electric field by connecting suitable electrodes to a conventional power supply. In operation, a suitably treated blood sample is loaded onto the top face of the agarose gel disc and, when the electric field is applied, the constituent parts of the treated blood, other than the DNA molecules, are drawn through the gel disc and are removed. The DNA is collected by interfacing the lower face of the gel disc with an open-ended elution or collection cup and deploying a dialysis membrane below the cup, typically having 50,000 molecular weight cutoff, the DNA sample being collected on such membrane.

A specific feature of the invention resides in an arrangement within the apparatus whereby the removal of the constituent molecules other than DNA is accomplished by initially positioning a gel disc sub-assembly at a first level within the electrophoresis buffer solution. An elution cup, forming part of the disc sub-assembly, is in this case spaced from the bottom of the gel disc, being held within a receptacle formed in a manifold sub-assembly. Consequently the molecules that are drawn from the gel disc by the electric field are swept away by the laminar flow of buffer solution that is then permitted through the manifold sub-assembly. However, when the gel disc sub-assembly is thereafter moved down, the DNA drawn from the gel disc directly enters the elution cup and is collected at the bottom on a membrane. At this point in the operation, the buffer solution cannot sweep away the DNA, there no longer being the space previously provided for flow of the buffer solution.

Other and further objects, advantages and features of the present invention will be understood by reference to the following specification in conjunction with the annexed drawing, wherein like parts have been given like numbers.

DESCRIPTION OF PREFERRED EMBODIMENT

Before proceeding with a detailed description of the preferred embodiment, it should be noted that the principle on which the present invention is based is that, in general, most particles carry a positive or negative charge. When a charged particle is introduced into an electric field, the particle experiences a force that moves it along the electric field lines towards one or the other of the electrodes producing that field.

If then, some kind of mechanical impedance is placed in the field—for example an agarose gel disc—the physically smaller particles will move through the impedance faster than larger particles. By suitably configuring the electrodes, agarose gels, electrical fields and operating times, it becomes possible to remove small particles and retrieve large particles. The judiciously selected elements in accordance with the present invention cause all molecules, other than DNA molecules, present in the blood sample, to be rapidly drawn through the agarose gel disc, whereby the DNA can be readily extracted as described heretofore.

In order to prepare a whole blood lysate for use in the invention, a lysis procedure was experimentally developed. The fundamental requirement is that the components of the lysate should be able to pass through the agarose gel disc without damaging the gel matrix. The DNA fraction should be of a molecular weight that will move slowly through the gel and be of a restrictable size. It will be understood that the proteins must be broken down to molecules of a size which can move rapidly through the gel disc. Furthermore, the lysate must be free of sediment. The blood lysis procedure consists in adding 0.5 ml. of whole blood with 4.0 ml. of DNA lysis buffer, such buffer consisting of 10 mM tris-HCl, pH 7.4, 10 mM NaCl, 10 mM EDTA (ethylenedianinetetraacetic acid). Further added to the whole blood and lysis buffer are 100 micrograms/ml. proteinase K and 1% SDS (sodium dodecyl sulfate). The components specified are mixed gently by inversion and are incubated at 37 degrees C. for two hours.

Gentle lysing of the kind just described insures that the DNA molecule is minimally sheared. Under certain electrode and field configurations very large DNA would cause damage to the gel disc. For this reason, prior to interfacing to the machine, the DNA is subject to a controlled shearing operation which reduces the size of the DNA molecules. These fragments pass through the gel disc without causing damage.

Figure 1:
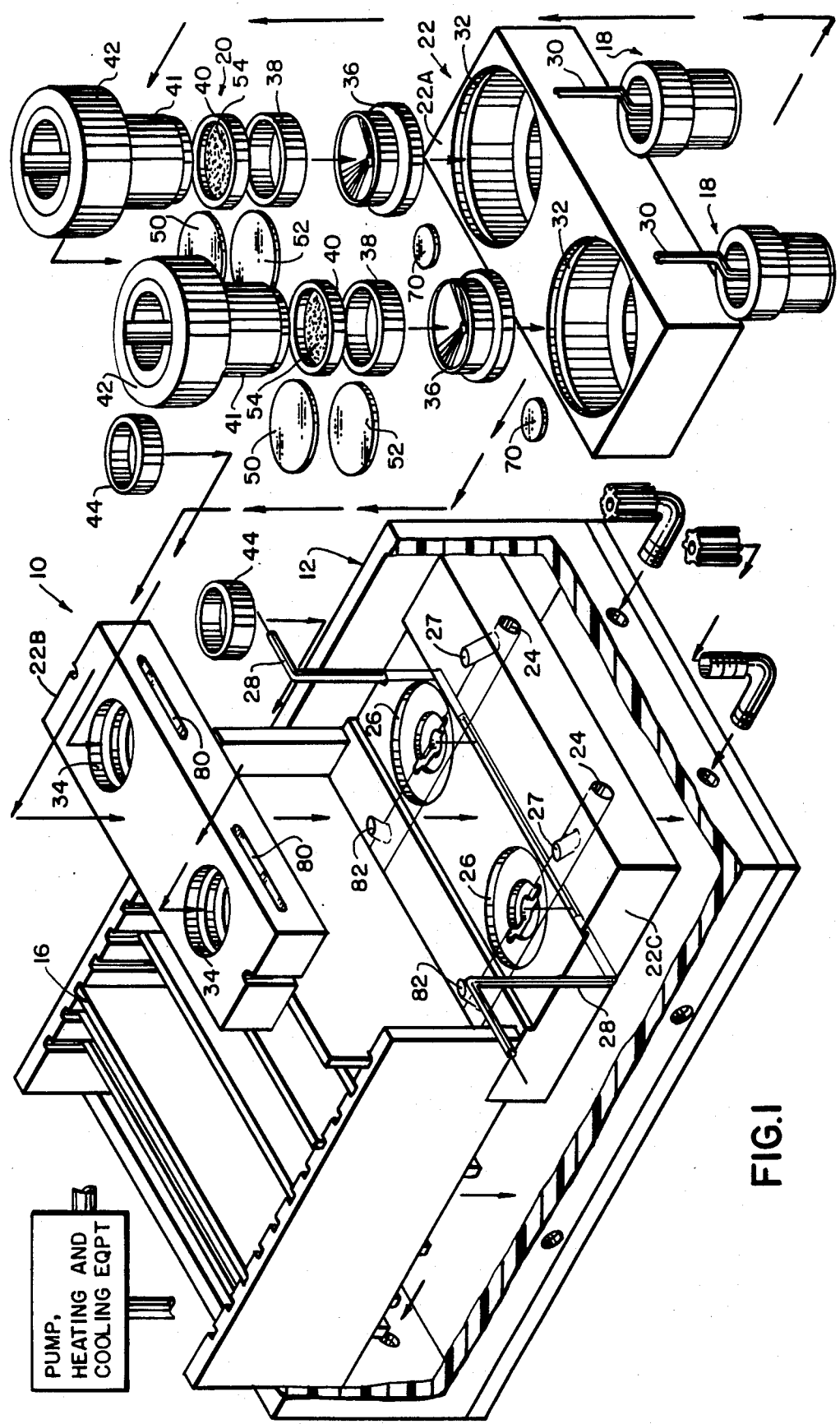
FIG. 1 is an exploded view of the apparatus in accordance with a preferred embodiment of the present invention.
Figure 2:
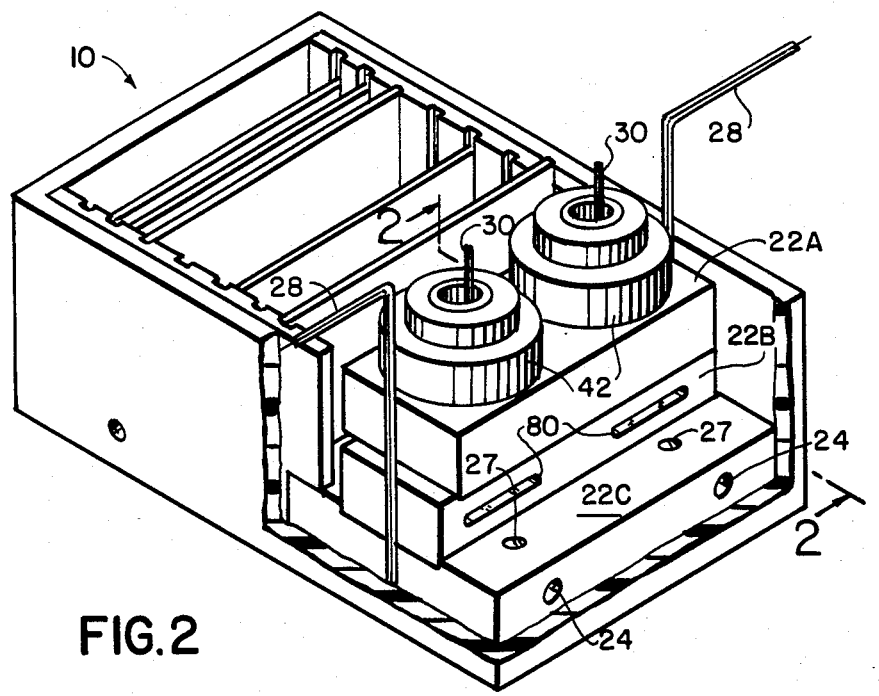
FIG. 2 is a perspective view of the principal components of that apparatus.

Referring to the figures of the drawing, that is, to FIGS. 1 through 6, there will be seen, particularly by first considering FIG. 1, an extraction apparatus or assembly 10 which includes the significant or essential components of applicants' invention. It will be understood as the description proceeds that heating and cooling equipment, and a recirculating pump (shown schematically in FIG. 1) as well as a suitable power supply, (not shown form part of the overall operating system for achieving the extraction of DNA from test samples.

The extraction apparatus 10 comprises a container 12 for containing a reservoir 14 (FIG. 3) in which is disposed a baffle means 16. Also contained within the container 12, as seen on the right, is the extraction assembly comprising a negative electrode sub-assembly 18, an agarose disc sub-assembly 20 and a manifold sub-assembly 22. The negative electrode sub-assembly 18 is adapted to fit into the top of the sub-assembly 20, the two components being partly received within sub-assembly 22. The latter includes a top manifold 22A, a bottom manifold 22B, and a bottom block 22C. In this bottom block there is disposed a piping system 24 which includes individual pipes for providing buffer flow to receptacle 26 in the bottom block 22C, and to bottom manifold 22B by means of apertures 27. Also provided in the bottom block 22C is the positive electrode 28 for purposes which will be apparent.

It will be seen that in the preferred embodiment, a dual arrangement is provided, that is, two mechanisms for extracting blood from two samples are incorporated in the system. Accordingly, it will be seen that a pair of electrodes 30 is included in the negative electrode sub-assembly 18 and that pairs of receptacles 32 and 34 are included in the top manifold 22A and bottom manifold 22B, respectively. Similarly, each of the disc sub-assemblies 20 includes corresponding elements. Thus, pairs of elution cups 36 for collecting the extracted DNA are provided; also, pairs of lower gel stops 38, as well as upper gel stops 40. At the top of this assemblage of elements are a pair of positioning sleeves 41 and sleeve locators 42.

All of the above described elements, that is, elution cups, upper and lower gel stops, and positioning sleeves and sleeve locators are adapted to be fitted within the receptacles 32. A pair of top and bottom locating sleeves 44 are designed to be placed, as indicated by the arrows, inside the receptacles of top and bottom manifold 22A, and 22B, respectively, thereby precisely locating top and bottom manifolds together.

Figure 3:
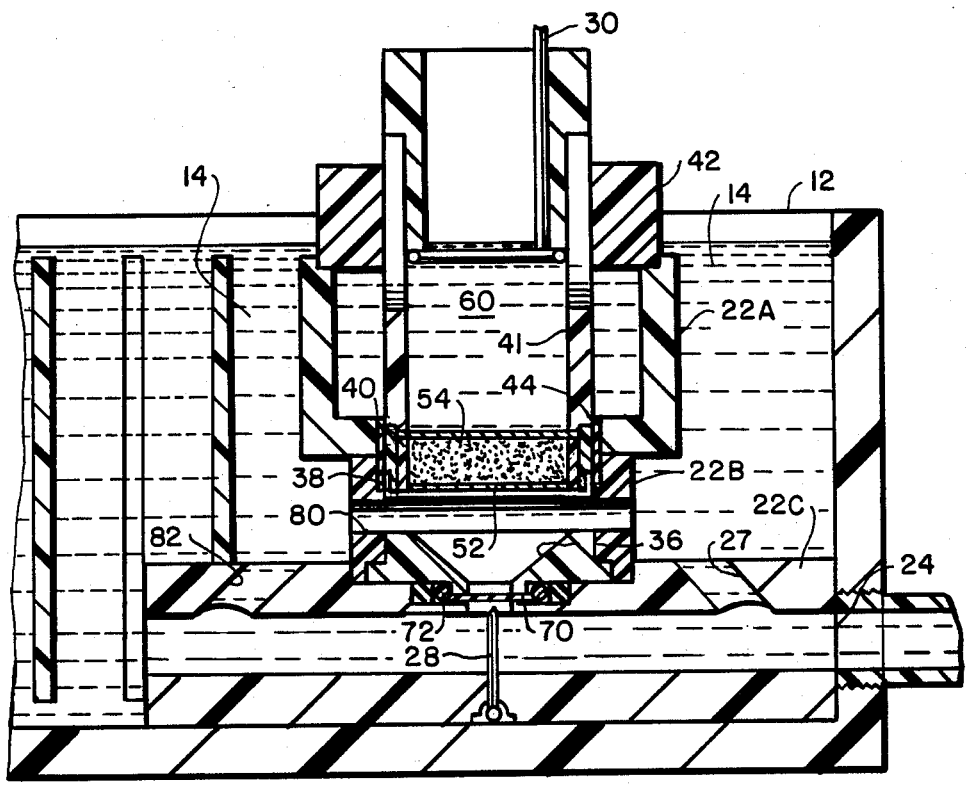
FIG. 3 is a sectional view, taken on the line 2—2, of the apparatus seen in perspective in FIG. 2, the gel disc being at a first level.
Figure 4:
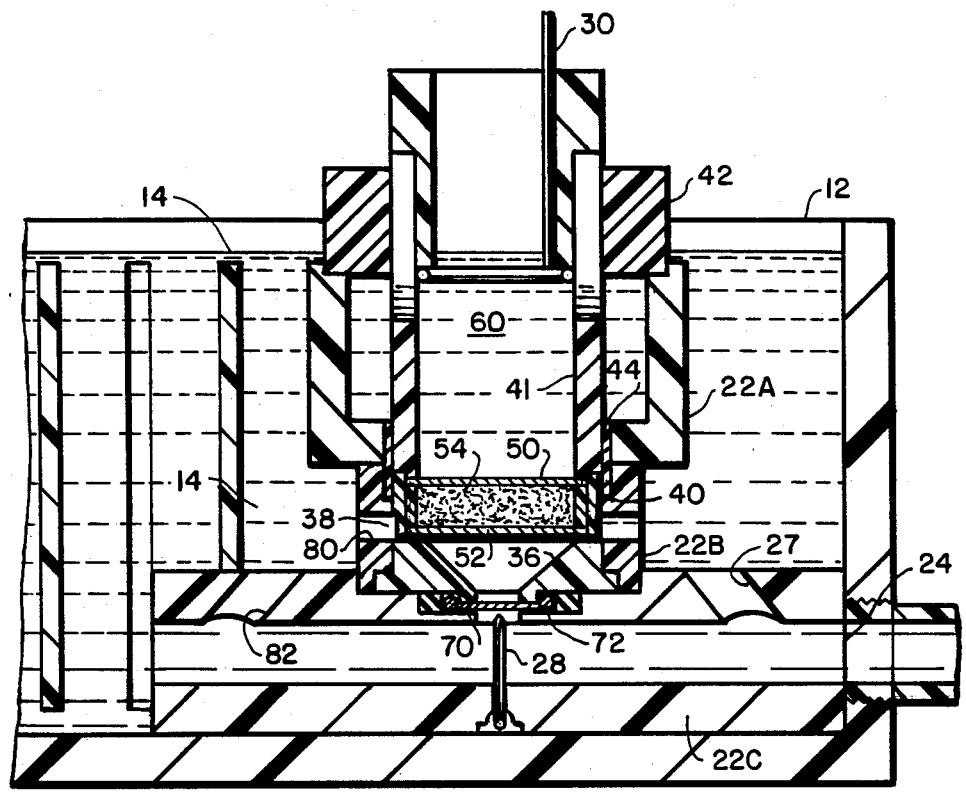
FIG. 4 is an identical sectional view, but with the gel disc at a second level.

The practice of the process in accordance with the present invention involves the use of a high purity agarose gel, such gel being in the form of a disc, which serves to minimize contamination of the DNA that might impede processing of the sample after recovery. Such gel disc is prepared by first placing a polycarbonate filter 50 against the end face of each of the positioning sleeves 41. Referring to FIG. 3 in particular, there will be seen the upper polycarbonate filter 50. In preparing the gel disc, the positioning sleeve 41 is of course in a reversed position from that seen in FIG. 3.

A casting plug previously chilled (not seen) is inserted within the bore of sleeve 41 so as to cool the gel when casting. An upper stop ring, that is stop ring 40, is placed over the filter 50 and is pressed down so as to clamp the filter in a stretched condition. The stop ring 40 then abuts a first shoulder adjacent the end face. The hot agarose gel is then dripped onto the filter 50, filling a well formed by the filter and the stop ring 40. The gel is then covered by another filter 52 imposed on top of the hot gel, which filter, in turn, is clamped by lower stop ring 38 against the outer periphery of the ring 40. The lower end of ring 38 abuts against a succeeding shoulder in the sleeve 41.

The gel disc which finally results is designated 54. The composition of this gel disc is preferably 0.5% high purity agarose in 1X Tris Borate. The latter has the composition: 90 mM Tris-HCl; 90 mM Boric Acid; 3 mM EDTA; pH 8.3.

It will be understood that the above noted percentages for the gel may be varied according to the amount of blood lysate to be loaded, and according to the electric fields used. Likewise, the thickness of the gel disc 54 may be varied. All of these factors predetermine the operating times to be used.

The reservoir 14 is filled with a buffer of the same composition as was used to prepare the gel disc; for example, 1X Tris Borate. Additional SDS and EDTA are added to help the disassociation of proteins and to minimize any harmful reactions between the DNA and iron. The buffer is mixed and recirculated through the apparatus 10 and is initially warmed to a nominal 32 degrees C., thereby increasing the mobility of the smaller constituent parts of the blood lysate through the gel disc.

The agarose disc sub-assemblies 20, comprising the aforenoted elements, that is, the positioning sleeves 41, the gel discs 54, the stop rings 38 and 40, and the elution cups 36, are loaded into the manifold 22 such that the recirculating buffer floods into the positioning sleeves 41 and submerges the gel discs 54. Any bubbles trapped under the gel discs are removed. The prepared blood lysate sample is then loaded onto the top of the gel discs. That is to say, two blood lysate samples are placed in the receptive chambers 60 defined at the interior of the sleeves 41 above the gel discs 54. Then, negative electrode sub-assemblies 18 are positioned on top of their respective positioning sleeves 41. A voltage is then applied across the positive and negative electrodes, thereby, at this stage, generating a uniform electric field across the full facial areas of the agarose disc.

In the operation of the apparatus, the blood lysate contained in the chambers 60 moves into the gel discs 54 under the effects of the electric field forces. At some predetermined time—when all the DNA is considered to have entered the gel discs—the electric field is removed and the buffer changed.

A flush step is now performed whilst continuing to maintain the temperature of the new, unpolluted buffer at a nominal 32 degrees C. The purpose of such step is to remove the blood particles from the gel discs 54 and to dilute any excess SDS and EDTA previously added to the now discarded buffer, but that may still be present on surfaces and in the gel disc within the assembled apparatus. During this step the positioning sleeve 41 of the gel disc sub-assembly 20 seen in FIG. 3 are at a position such that laminar flow from aperture 27 is able to sweep through a slotted openings 80 in bottom manifold 22B and exit by way of apertures 82 in block 22C.

Because of the buffer recirculation, blood particles moving into the buffer may be carried back into the gel. Therefore, a second flush step is required at an increased level of electric field. In this step fresh buffer is used to dilute further any contaminating particles remaining in the buffer.

After the second flush step, the gel discs 55 are clear of visible heme and other contaminants and predominantly contain the DNA from the blood lysate. The buffer is again replaced, and the lower face of the gel discs are interfaced with their respective elution cups 36. As will be seen in FIG. 4, the positioning sleeve 41 has now been pushed down from its previous position in FIG. 3 to achieve this interfacing. As a consequence, the previously described laminar flow path through slotted opening 80 is blocked. Associated with each of the elution cups 36 at a level below them is a dialysis membrane 70. The dialysis membrane is placed in position below an opening in the elution cup 36 and secured by an "O" ring 72 and plastic clamp ring 74.

The elution step of the procedure is then run, involving cooling the buffer and maintaining its temperature at a nominal 22 degrees C. For this step the potential across the electrodes is increased to 100 volts, thereby driving the DNA from the gel discs at an increased speed into the elution cups. The samples of DNA suspended in the buffer, in contact with, and directly above the dialysis membranes 70 affixed to the bottoms of the elution cups 36, are then recovered in a small usable volume.

An essential feature of the invention, namely the gel discs, require several support systems to ensure that the apparatus operates in a known and repeatable manner. Primarily, the system requires that the electric field, which draws the lysate through the gel, be repeatable between consecutive extractions. This field could change unpredictably if: (1) the pH of the buffer were to vary beyond acceptable limits in the vicinity of the electrodes, (2) the impedance of the path in the electric field were to change because of gas bubble collection, and (3) if the temperature of the buffer were to vary beyond acceptable limits.

The buffer used is 1X Tris Borate whose composition has been described previously. This buffer is considered to be a "strong" buffer in that it will closely maintain a constant pH when exposed to electrodes that are conducting an electric current. Constant recirculation of the buffer into a large volume minimizes localized pH changes. The apparatus 10 is configured such that a flow moves over each of the lower, positive electrodes and the buffer is recirculated into the large reservoir 14. There is no flow over the top negative electrode. Therefore, the volume of buffer in receptacles 32 and 60 has to be large enough to maintain an acceptable pH level above the gel disc. Any flow in this upper volume may disturb the lysate above the gel disc and may recirculate large amounts of unwanted material above the gel discs, thereby prolonging the machine's operating time.

Because of the vertical configuration of the apparatus as seen in the figures, gas bubbles generated at the lower positive electrode rise and collect under the gel discs 54 and subsequently, during the elution stage, under the dialysis membrane 70. A large buildup of gas at either of these two interfaces would effectively reduce the current flowing between electrodes and produce unrepeatable voltage differentials at unspecified positions in the system.

To prevent the accumulation of bubbles, the buffer is pumped rapidly over the lower, point electrode 28. This flow carries gas generated there into the large reservoir 14, where the baffle means 16 enables the gas to escape into the atmosphere, instead of being recirculated back to the manifold 22.

The power dissipated into the gel discs and the buffer would in time, particularly during the elution phase where the electric field is more intense, produce a temperature rise, which could damage the gel and the DNA. To remove heat during this phase, the buffer is recirculated through a closed loop cooling heat exchanger. The recirculation maintains a temperature equilibrium within the apparatus.

The intensity of the electric field during the run and flush stages is lower than during the elution phase, resulting in a reduced power dissipation into the buffer and gel during the run and flush. For this reason, the buffer is heated by external heat exchange during the first two stages of operation, to enhance the passage of small blood lysate particles through the gel. The movement of the larger DNA through the gel is less affected by this heating.

To enable one skilled in the art to thoroughly appreciate and practice in detail the technique of the present invention, a DNA extraction and measuring protocol is herewith provided:

1. Place casting plugs on ice.
2. Cut a $\frac{3}{4}'' \times \frac{3}{4}''$ square piece of 50k molecular weight dialysis membrane into a single layer. Pretreat with dH20.
3. Prepare a 0.5% high purity agarose (International Biotechnologies, Inc.). Mix 0.125 g in 25 ml buffer.
4. Cast gels -
   A. Place positioning sleeve over cooled casting plug.
   B. Lay an 8 micrometer polycarbonate membrane on top of casting plug.
   C. Slip on upper gel stop, thereby pretensioning the membrane.
   D. Using a plastic transfer pipette, put gel onto membrane until a slight meniscus forms above the upper gel stop. (Some of the gel may leak down plug, wait a few seconds before placing other membrane. Reform the meniscus, if necessary, to prevent air bubbles from forming.)
   E. Carefully place another 8 μm polycarbonate membrane over gel, position layer gel stop. Again, make sure membrane is smooth and pretensioned. It should not be concave.
   F. Place in 4 degrees C. refrigerator until set.
5. Pour 2 liters 1X Tris Borate (TB) in reservoir. Turn on pumps.
6. Add 0.2% of 20% sodium dodecyl sulfate (20 ml SDS) and 10 mM ethylenediaminetetraacetic acid (36 ml 0.5M EDTA), let circulate 10 minutes before placing gels. Fill heating/cooling apparatus with warm water to maintain buffer temperature at 30°-34 degrees C. during run and flushes.
7. Place pre-cut and pretreated dialysis membrane on elution cup well, secure with "O" ring and plastic ring, make sure membrane is tight. (Vaseline may be needed around the inside of the plastic ring to keep from popping up.) Place in bottom block of machine, position bottom and top manifolds using locating sleeves.
8. Lysate preparation -
   A. Pipette 2.5 ml lysed blood into 10 ml tube.
   B. Vortex 10 seconds at #10.
9. Remove casting plugs from refrigerator. Carefully pull out plug, wipe away any excess gel from inside with Kimwipe. Slip locator sleeve on end of positioning sleeve, even off against smooth surface.
10. Position sleeves in top manifold. Outer buffer level should be slightly lower than manifold; if too high, reverse pumps to drain some buffer out. If buffer in cell is too low, use plastic transfer pipette to fill with buffer from reservoir.
11. Place negative electrodes in positioning sleeves. Turn on power supply. (Electrodes should not be connected.)
12. Using plastic transfer pipette, put 2.5 ml lysate in each cell. Pipette should be as close to gel as possible beforre dispensing to prevent lysate from dissipating into buffer.
13. Set voltage (40 volts) with voltmeter. Turn on recorder. Connect negative electrodes, make sure the electrodes are flush with the top of the positioning sleeve.
14. Record date, experiment number, time, volts and milliamps on recorder. Run for 1 hour.
15. Disconnect power supply. Record time on recorder. Reverse pumps to drain buffer. Remove negative electrodes and sleeves. Rinse with 1X TB.
16. Add 2 liters 1X TB to reservoir, adjust level of buffer. Turn on pumps, replace sleeves and negative electrodes.
17. Set voltage to 50 volts. Connect power supply. Record time, volts and milliamps on recorder. Flush for 30 minutes.
18. Repeat steps 15-17 for flush #2, except, let run until lysate is out of gel.
19. Repeat step 15. Remove positioning locators. Replace warm water in cooling apparatus with ice. (Elution buffer is maintained at a nominal 22 degrees C.)
20. Add 1X TB buffer; adjust level. Turn on pumps. Place positioning sleeves into cells and push down to snap into elution cups.
21. Set voltage to 100 volts; connect power supply. Record time, volts and milliamps on recorder. Let run 2 hours.
22. Turn off power supply and recorder. Record time on recorder. Reverse pumps to drain buffer. Carefully remove top and bottom manifolds; remove sleeves and elution cups as one piece.
23. Remove gel from between membranes; nick top with razor blade. Stain with ethidium bromide (100 μg/ml) for 10 minutes. Destain with 1X TB for 10 minutes. Cut transverse section through gel and photograph over UV light.
24. With plastic transfer pipette, remove top buffer from elution cup. Discard. With wide-ended pipette tip, remove DNA sample from membrane. Place in 0.5 ml Eppendorf tube. Label with experiment number and volume collected. Store at 4 degrees C.

Four typical runs, involving eight samples, that were conducted in accordance with the protocol set forth above, produced samples of DNA having the following volumes and yields:

| Sample # | Volume (micro l) | Yield (micro g) |
| --- | --- | --- |
| 192F | 50 | 2.4 |
| 192B | 60 | 14.9 |
| 193F | 55 | 17.8 |
| 193B | 75 | 17.0 |
| 194F | 60 | 10.4 |
| 194B | 75 | 12.3 |

| Sample # | Volume (micro l) | Yield (micro g) |
|---|---|---|
| 195F | 55 | 11.2 |
| 195B | 45 | 15.9 |

While there has been shown and described what is considered at present to be the preferred embodiment of the present invention, it will be appreciated by those skilled in the art that modifications of such embodiment may be made. It is therefore desired that the invention not be limited to this embodiment, and it is intended to cover in the appended claims all such modifications as fall within the true spirit and scope of the invention.

We claim:

1. Apparatus for purifying and concentrating DNA from a crude mixture containing the DNA comprising:
   a container providing a reservoir of electrophoresis buffer solution;
   a gel matrix immersed in said electrophoresis buffer solution;
   a collection chamber in said container;
   means for applying an electric field to said gel matrix;
   means for disposing said crude mixture in contact with the gel matrix such that the crude mixture is drawn into the gel matrix, responsive to said electric field;
   means for selectively removing, due to their relatively low molecular weight, all the constituent molecules of the crude mixture, except for the DNA, from said gel matrix responsive to said electric field, including means for sweeping away said constituent molecules by flow of said electrophoresis buffer solution between the bottom of the gel matrix and the collection chamber; and
   means for removing from the gel matrix, responsive to said electric field, the DNA still remaining therein such that the DNA is collected in said collection chamber, including means operative when removing the DNA for preventing said flow of said electrophoresis buffer solution, thereby to avoid sweeping away the DNA.

2. Apparatus as defined in claim 1, in which said crude mixture is human whole blood which has been treated.

3. Apparatus as defined in claim 2, in which said crude mixture is human whole blood which has been mixed with a lysis buffer.

4. Apparatus as defined in claim 1, further comprising an extraction assembly, and in which said means for applying an electric field includes a positive electrode and a negative electrode connected to spaced locations on said assembly.

5. Apparatus as defined in claim 4, in which said extraction assembly comprises a gel disc sub-assembly and a manifold sub-assembly, said positive electrode being connected to said gel disc sub-assembly and said negative electrode to said manifold sub-assembly.

6. Apparatus as defined in claim 5, in which said positive electrode is a point electrode located near the bottom of said extraction assembly.

7. Apparatus as defined in claim 6, further including means for preventing the accumulation of bubbles adjacent said positive, point electrode by pumping the buffer solution rapidly over said electrode.

8. Apparatus as defined in claim 5, in which said gel matrix is an agarose gel disc and two filters, and said manifold sub-assembly includes a top manifold, a bottom manifold, and a bottom block.

9. Apparatus as defined in claim 8, in which said bottom manifold is provided with an opening for said flow of buffer solution in sweeping away said constituent molecules.

10. An apparatus as defined in claim 1, in which said gel matrix has an upper face and a lower face, and further in which said means for disposing the test sample enables contacting said upper face of said gel matrix with said sample.

11. Apparatus as defined in claim 1, in which said means for selectively removing includes means for initially positioning said gel at a first level within said electrophoresis buffer solution.

12. Apparatus as defined in claim 11, in which said means for removing the DNA from the gel matrix includes means for positioning said gel matrix at a lower level than said first level.

13. Apparatus as defined in claim 12, in which said applied electric field has a first value when said gel matrix is positioned at said first level, and said electric field has a second value when said gel matrix is at said lower level.

14. Apparatus as defined in claim 13, including means for preventing the DNA from being swept away by the flow of electrophoresis buffer solution, while applying an electric field sufficient to remove the DNA from the gel, whereby the DNA is collected for further testing.

* * * * *

UNITED STATES PATENT AND TRADEMARK OFFICE
CERTIFICATE OF CORRECTION

PATENT NO. : 4,617,102

DATED : October 14, 1986

INVENTOR(S) : Tomblin et al.

It is certified that error appears in the above-identified patent and that said Letters Patent are hereby corrected as shown below:

In The Specification

Column 6, line 3, change "55" to --54--

Signed and Sealed this

Tenth Day of February, 1987

Attest:

DONALD J. QUIGG

Attesting Officer

Commissioner of Patents and Trademarks